United States Patent [19]

Teets et al.

[11] Patent Number: 5,427,144
[45] Date of Patent: Jun. 27, 1995

[54] VALVE MEANS WITH FLUID RETRACTION MEANS

[75] Inventors: J. Michael Teets, Hobe Sound; Bruce E. Wiita, North Palm Beach; Gregory D. Witta, Palm Beach Gardens, all of Fla.

[73] Assignee: Deumed Group Inc., Palm Beach Gardens, Fla.

[21] Appl. No.: 201,287

[22] Filed: Feb. 24, 1994

[51] Int. Cl.$^6$ ............................................ F16K 3/24
[52] U.S. Cl. .................................. 137/614.2; 251/324; 222/571
[58] Field of Search .................. 137/614.2, 513.3; 251/282, 324; 222/571

[56] References Cited

U.S. PATENT DOCUMENTS

| | | | |
|---|---|---|---|
| 1,565,686 | 12/1925 | Titus | 222/571 X |
| 3,160,331 | 12/1964 | Trumbull et al. | 222/571 X |
| 3,349,973 | 10/1967 | Smith | 222/571 X |
| 5,131,425 | 7/1992 | Sturgis | 137/614.2 X |
| 5,228,646 | 7/1993 | Raines | 251/324 X |
| 5,313,934 | 5/1994 | Wiita et al. | 128/4 |

*Primary Examiner*—Stephen M. Hepperle
*Assistant Examiner*—Kevin L. Lee
*Attorney, Agent, or Firm*—Norman Friedland

[57] ABSTRACT

A combined trumpet valve and reed valve serve to control the flow of fluid into a conduit and is particularly adapted for lens cleaning apparatus for flowing water over the lens or lens cover in an endoscope with viewing mechanism and is capable of retracting the trapped fluid in the conduit to prevent it from dripping into the area being viewed and removing any residual fluid that is left on the lens when the valve is positioned to the closed position.

15 Claims, 8 Drawing Sheets

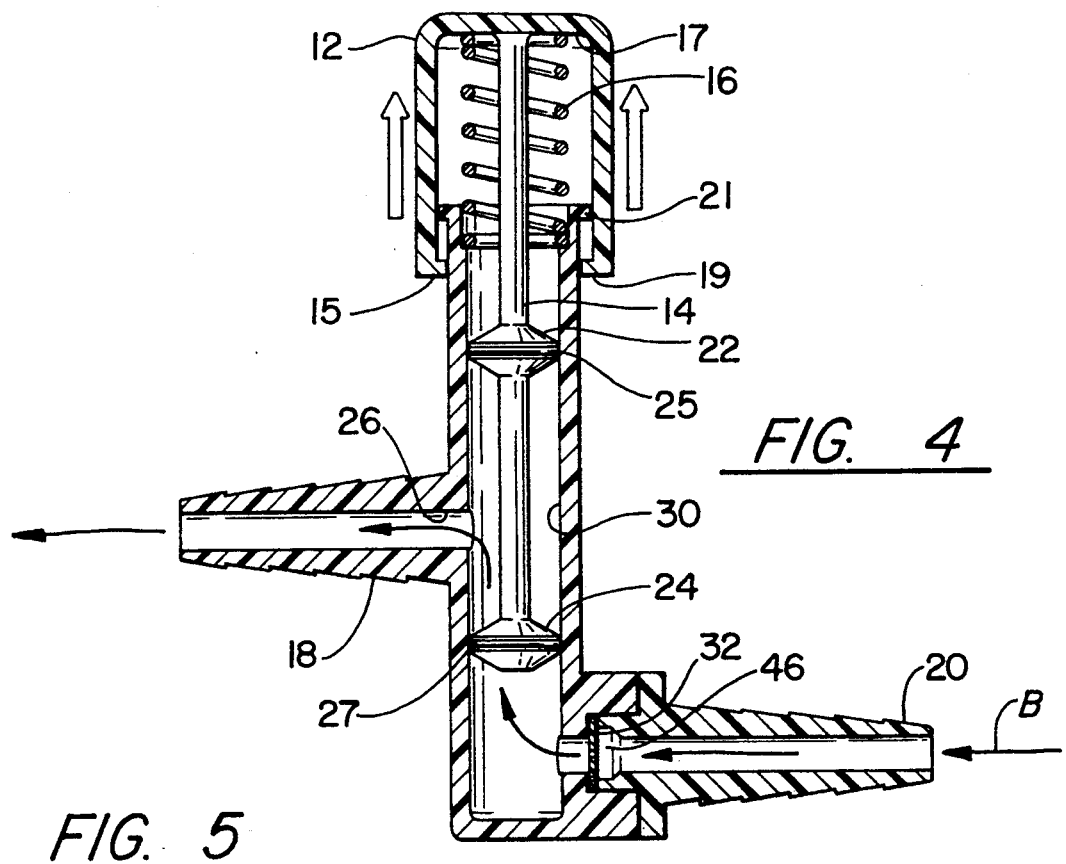
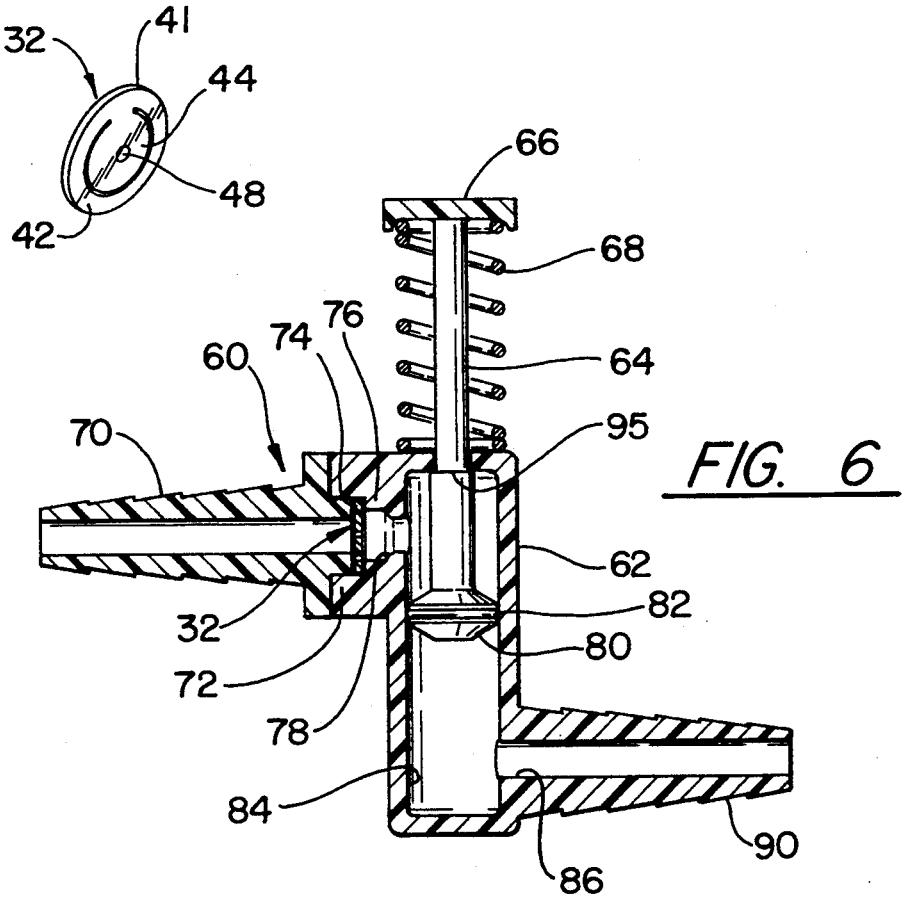

VALVE MEANS WITH FLUID RETRACTION MEANS

CROSS REFERENCES

This invention relates to the subject matter disclosed in U.S. patent application Ser. Nos. 07/943,315 filed on Sep. 10, 1992 and 08/014,436 filed on Feb. 5, 1993 both of which are asssigned to DEVMED GROUP INC. the assignee of this patent application.

1. Technical Field

This invention relates to valves and particularly to valve means that open and shut-off the flow of a non-compressible fluid flowing into a tube or the like that is capable of retracting a portion of the residual fluid trapped in the tube or the like after the valve is shut-off and the combination of the valve means and tube.

2. Background Art

As is well known, there are certain application where the flow of fluid is turned on and off by a value and it is important that the residual fluid in the tube downstream of the valve is prevented from dislodging and discharging from the tube into the environment where it is unwanted when the valve stops the flow of fluid. Further, in an environment that uses a lens, a valve and fluid flowing means for flowing fluid for cleaning the lens it is equally important to remove any fluid left on the lens. When employing video endoscopes used in laproscopic, cystocopic, anthroscopic, surgery or used for pelviscopy, for example, it is desirable to cleanse the lens of the video camera periodically and prevent the inadvertent dripping of water into the area adjacent the lens while the lens cleaning function is turned off.

Hence, during the performance of an operation or a visual inspection of the internal parts of a body, the lens cleaning system is turned on and off intermittently and when in the nonflowing condition, there is a propensity for a drop of the residual fluid trapped in the flow line(s) of the system to discharge from the discharge end which tends to migrate toward the lens and impair the vision of the viewer. In copending application Ser. No. 07/743,315, filed on Sep. 10, 1992, now issued as U.S. Pat. No. 5,313,934 for example, water is used to cleanse the lens of a video camera utilized in laproscopic surgery and the like, and capillary action within the flow passages is relied upon to remove the residual fluid from the cleansing system. In this instance, a trumpet valve serves to turn the flow on and off and the retraction of the residual fluid trapped in the tube is predicated on the tube configuration. As this particular design relies on capillary action of the fluid within the tube to cause the fluid to retract in order to prevent a droplet of fluid to inadvertently drop off and/or migrate to the camera lens and cause a distortion of the image being viewed, it is important that the system is manufactured with precision dimensions in order for it to work satisfactory.

Further, since the precision dimensions are predicated on other components in the system that are obtained from various manufactures it is difficult to maintain adequate tolerances necessary to obtain the capillary action to perform this function, This invention contemplates performing the retraction of the residual fluid trapped in a tube or tube-like environment by incorporating into the trumpet valve a reed valve and designing the trumpet valve with a certain stroke and suction creating means that will cause the residual fluid trapped in the system to be retracted away from the discharge end and eliminate or minimize the propensity of a droplet from inadvertently dislodging.

SUMMARY OF THE INVENTION

An object of this invention is to provide valving means for controlling the flow of fluid that has on/off capabilities and means for retracting fluid trapped in the flow line downstream of the valve when the valve is in the off position, A feature of this invention is the inclusion of a reed valve in combination with an on/off spool valve that includes a plunger having a Judiciously dimensioned stroke that sequentially closes the valve and creates a suction to retract the trapped residual fluid downstream of said valve.

Another feature of this invention is a reed valve that has restricted flow in one direction and unrestricted flow in the opposite direction disposed in serial fluid relationship with a spool valve.

Another feature of this invention is the utilization of a combined trumpet valve and reed valve with a judiciously dimensioned stroke in serial fluid communication, This combination yields a defined volume of fluid retraction displacement at a controlled rate and maintenance of all fluids in constant communication with the main body of fluid and assures no fluid shear separation.

Another feature of this invention is the improved lens cleansing means for medical viewing instruments in combination with the combined trumpet and reed valve for retracting residual fluid trapped in the cleansing means. The lens cleaning means includes a handle for releasably supporting an endoscope with video capabilities and the trumpet/reed valve being mounted in the handles and a self-contained cleaning system including an attached lens for encasing said endoscope.

The foregoing and other features of the present invention will become more apparent from the following description and accompanying drawings.

BRIEF DESCRIPTION OF DRAWINGS

FIG. 4 is a sectional view in elevation, of the valve depicted in FIG. 2 when in the retracting mode and the valve is closed;

FIG. 5 is a plan view of the reed valve utilized in trumpet valve embodiments depicted in this patent application;

FIG. 6 is a sectional view in elevation of another embodiment of this invention illustrating the valve in the normally closed position;

BEST MODE FOR CARRYING OUT THE INVENTION

Figure 1:
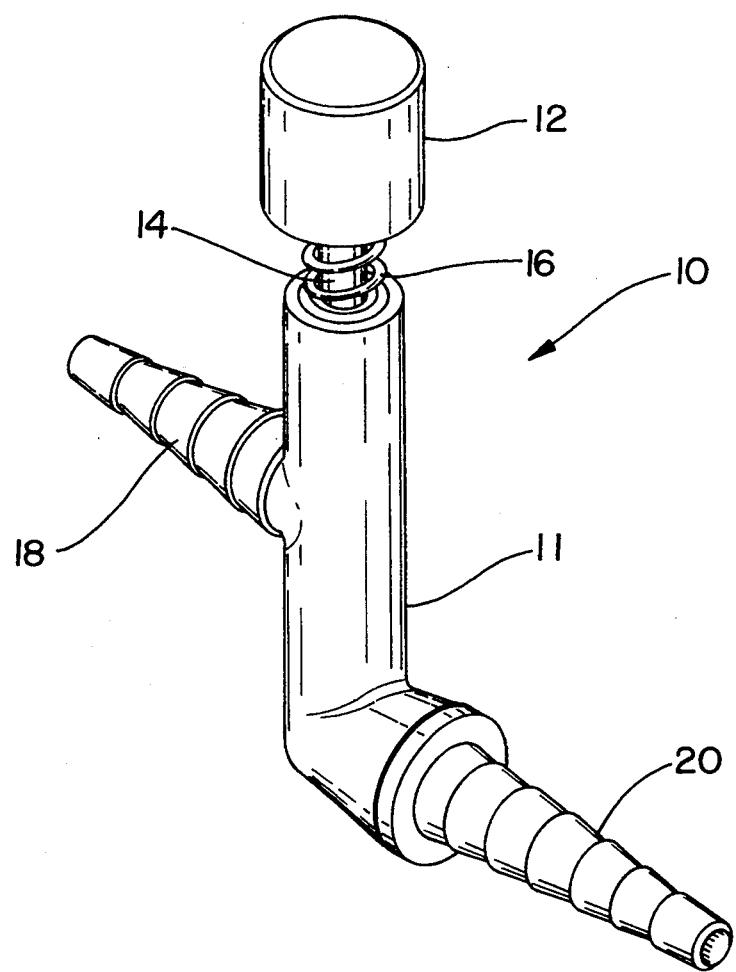
FIG. 1 is a perspective view of the valve of this invention.

In the context of this description, the term valve when describing this invention is defined as the combination of a trumpet type valve in combination with a reed valve or its equivalent and their being in serial fluid relationship relative to each other. The reed valve can take the form of any check valve that is opened in one direction and closed in the other. The reed or check valve configuration would include a small orifice or groove either in the movable valve element or the adjacent valve seat to allow a small amount of flow in the reverse direction.

The invention can best be understood by referring to FIGS. 1-5 which shows the valve generally indicated by reference numeral 10 as comprising a main valve body 11, plunger cap or handle and spring retainer 12, plunger or valve stem 14, coiled spring 16, tapered inlet nipple 18 and tapered outlet nipple 20. Nipple 18 may be formed integral with the valve body and nipple 20 is a separate, detachable element that is attached to the valve body 11 to define the housing for the reed valve as will be described in further detail hereinbelow. The nipples are tapered and/or stepped in order to accommodate the connecting hoses or tubes to connect the valve between the source of fluid and its output or the receiver of the fluid. The stepped version are formed with incremental cylinders to form a cone allowing adhesive retention cavities. It is of course understood that other types of fluid connectors such as clamps may be equally employed. Valve body 11 includes an upper end 13 and an enclosed lower end 15 so that fluid from the inlet 18 enters the central bore or chamber 30 of valve body 11 and flows out through the outlet 20 as will be described in further detail hereinbelow.

As mentioned above the valve is a normally closed valve and is opened by depressing the handle 12 similarly to a trumpet valve. The depressing of handle 12, in turn, forces the attached plunger stem 14 which may be integrally formed therewith, to position the axially disposed lands 22 and 24 integrally formed on the plunger stem 14. The upper end of stem 14 extends through an opening formed in the upper end 13 where it is attached to or formed a part of the handle 12. Coil spring 16 is seated at the upper end 13 of the valve body 11 and the retainer 17 formed by the handle 12.

As is apparent from FIGS. 1-4 the valve body 11 defines a cylindrical central chamber 30 that is in fluid communication with inlet port 26. Fluid enters chamber 30 and is confined between lands 22 and 24. O-rings 25 and 27 or other seal members may be attached to complementing annular groove:3 formed in the outer periphery of the lands 22 and 24 to be in sliding relationship with the wall of chamber 30 to form a seal between the confined space between the lands and the upper and lower portion of the chamber 30. As noted in FIG. 3 the positioning of lands 22 and 24 to the bottom of the chamber 30 places the inlet port 26 in fluid communication via chamber 30 with the outlet port 28 formed on the bottom of valve body 11.

In accordance with this invention, the reed valve generally illustrated by reference numeral 32 is mounted in the small space provided between the shoulder 36 of valve body 11 and the end face 38 of outlet nipple 20. Reed valve 32 is fabricated from a plastic flexible material such as polyvinylchloride or other synthetic material and is a circular shaped thin, flat member 41 having the central portion 44 cut along an arcuate path and fixed at one end so that the central portion can flex in and away from the peripheral portion or as view from FIG. 5 into and out of the plane of the paper. However, when mounted into the space as described the central portion 44 is constrained in one direction and unrestrained in the other. As noted in FIG. 3, the face 40 of shoulder 36 and the face 38 when the nipple 20 is assembled clamps the outer periphery 42 of reed valve 32. The diameter of outlet port 28 is slightly smaller than the outer periphery 42 so that the material surrounding port 28 extends inwardly a slight distance to bear against a portion of periphery 42 to restrict inward movement so that the central portion 44 can only move to the open position by flexing into the increased diameter of cavity 46 formed in the inner end of outlet nipple 20.

Figure 3:
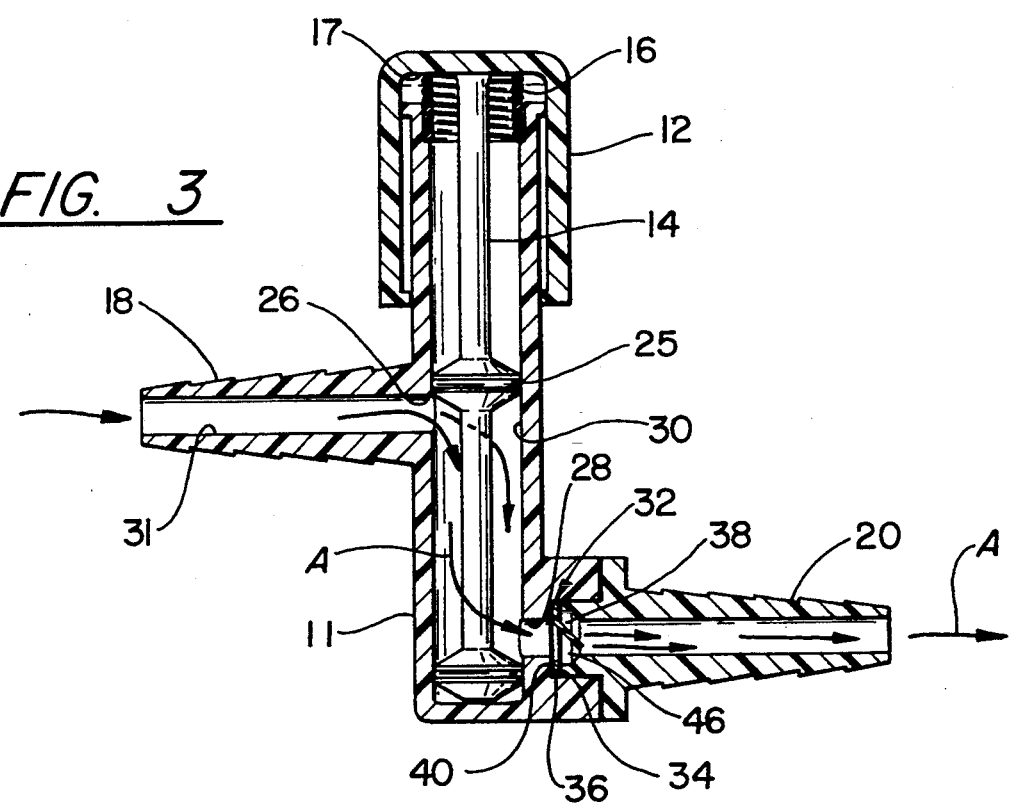
FIG. 3 is a sectional view in elevation with the valve fully depressed in the open position.

Hence when flow is in the direction illustrated by arrow A in FIG. 3, i.e., when the valve 10 is in the open position, flow is permitted to egress through the outlet nipple 20 without restrictions and the reed valve is forced by the pressure exerted by the egressing fluid to flex to the open position.

However, when the flow is flowing in the reverse direction as illustrated by arrow B, by releasing the handle so that it will be retract by the force generated by spring 16 the center portion 44 of reed valve 32 is forced against the face of the adjacent shoulder to close off the flow. A small pin hole 48 formed in the central portion of the reed valve 32 or by designing the reed valve 32 with sufficient tolerances to allow a small amount of leakage around its seating area serves to flow the fluid at a reduced rate in the opposite direction. Obviously, the rate of flow in the reverse direction is restrained to a lower value than it would be if allowed to flow without any restriction.

It is apparent from the foregoing that this restriction limits the rate of flow of the fluid being retracted. This is to assure that a rapid flow of fluid won't cause a separation of the column of residual fluid that is trapped in the hose or tube downstream of the valve 10.

As noted FIG. 4, as the valve is retracted and valve stem 14 moves upwardly by virtue of the spring 16, land 24 crosses over the outlet port 28 breaking the communication between the outlet port and inlet port, or in other words closes the valve 10. However, valve stem 14 continues its upward travel increasing the volume in the lower portion of chamber 30. As noted valve stem translates as far up to the point where the upper portion of land 22 comes into contact with the valve body 11. This movement causes a vacuum or suction in the lower portion of chamber 30 and retracts the flow in the outlet into this cavity portion through the pin size orifice in the reed valve 32. Since the flow in the reverse direction can only flow through the pin size orifice 48, the flow will be restricted which, in turn, restricts the velocity of the valve stem in its upward travel and retracts the residual fluid trapped in the downstream hose or tube through the lower portion of chamber 30 that is being evacuated by the movement of land 24. This has the effect of withdrawing the residual fluid at the end of the hose or tube from its outlet end and avoiding the tendency for drops of fluid from becoming dislodged from this end.

The depressible handle 12 depicted in FIGS. 1–4 is fabricated from a plastic flexible and resilient material such as polyvinylchloride or the like and is removable to gain access internally of the valve body 11. Depressible handle 12 is opened at the bottom end and closed on the top end and includes a central recess. A pair of projections 15 and 19 extend radially inward toward the valve stem 14 attached to the inner surface of the top end of handle 12. The upper end 13 of the valve body 11 is formed with an outward extending annular lip 21. The lip 21 act as a stop and prevents the cap from dislodging. By squeezing the sides of the cap at a location away from projections 15 and 19 causes the cap to assume an elliptical shape whose major axis is longer than the diameter of the lip 21 allowing the handle to be extracted.

Figure 7:
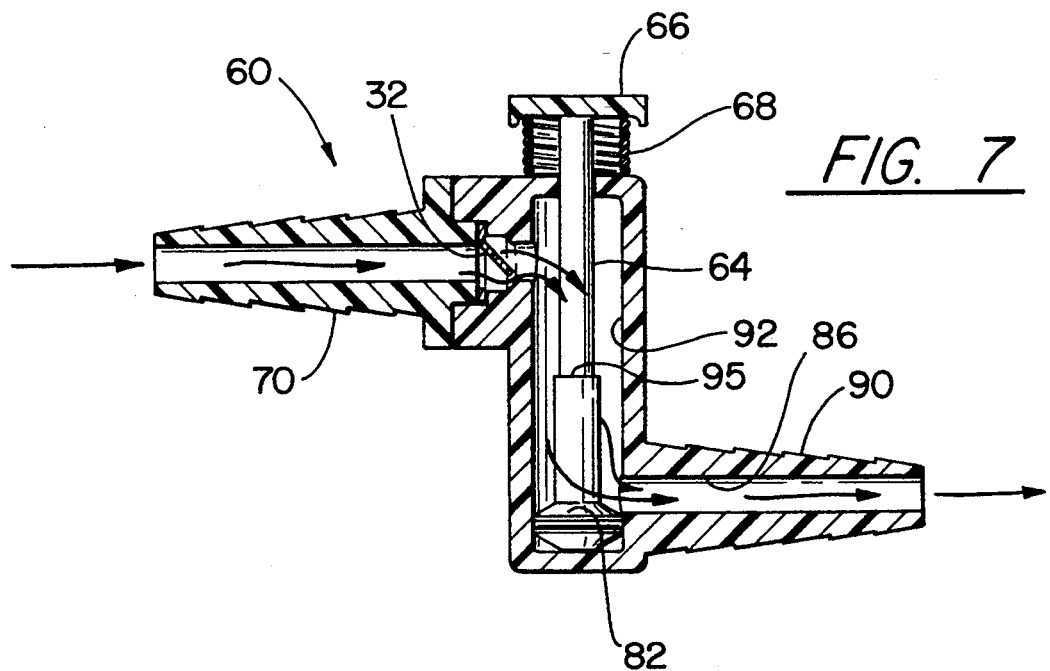
FIG. 7 is a sectional view in elevation of the valve depicted in FIG. 6 when in the opened position.
Figure 8:
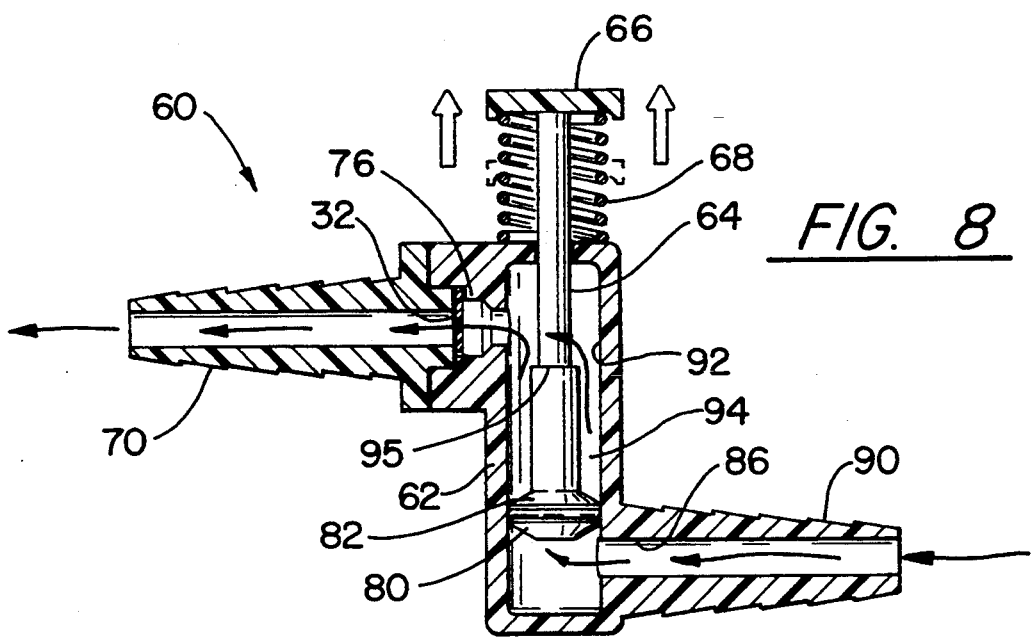
FIG. 8 is a sectional view in elevation of the valve depicted in FIG. 6 illustrating the valve in,the closed position and in the retraction mode.

FIGS. 6–8 exemplifies another embodiment of this invention where the reed valve is mounted in the inlet rather than the outlet. In this embodiment as best seen in FIGS. 5–8, (like elements depicted in all the Figs. bear the same reference numerals) the valve generally illustrated by reference numeral 60 includes valve body 62 shaped similar to valve body 11 in FIG. 1. Valve stem 64 disposed in chamber 84 extends through an opening formed at the top of valve body 62 and includes the integral cap and spring retainer 66. Coil spring 68 seated on the top end of valve body 64 and retained by retainer 66 is biased in the upward direction to normally hold the valve in the closed position.

As mentioned above, the reed valve 32 (FIG. 5) is housed in the inlet port and is retained in place by inlet nipple 70 which is a separate and detachable element. The outer periphery 42 of reed valve 32 is clamped between the end face 72 formed at the inner end of nipple 70 and the face 74 of shoulder 76 formed adjacent to the inlet port 78 of valve body 62. The inlet port is tapered and is larger in diameter at the entrance end adjacent the reed valve 32 to allow the central portion 44 to flex therein The taper is for ease of manufacturing as all that is required is sufficient space to allow the reed valve to flex open. Obviously, inlet flow, when the valve 60 is positioned to the opened position, is allowed to enter the chamber 94 unrestricted. This is demonstrated in FIG. 7.

To place the valve from the closed position as depicted in FIG. 6 to the open position as depicted in FIG. 7, the cap 66 is depressed to force valve, stem 64 toward the bottom of valve body 62. Land 80 integrally formed on valve stem 64, like lands 22 and 24, and which may include an O-ring formed in an annular groove therein, is in sliding relationship with the wail defining the cylindrical chamber 94 formed in valve body 52. When fully depressed land 80 is position beyond outlet port 86 which leads fluid into outlet nipple 90 placing the inlet port 72 in fluid communication with outlet port 86 via annular passageway 92.

When closing valve 60, the cap 66 is released and spring 68 forces the valve stem 64 in the upward position moving land 80 to cross over outlet port 86 to block off the flow of fluid from inlet port 72. As is apparent from FIG. 8 once past outlet port 86, the land continues to move upwardly to increase the volume of the lower portion of chamber 94. Obviously, valve stem 64 continues its upward travel until the shoulder 94 formed by the increased diameter portion of valve stem 64 contacts the upper end of valve body 62 at the upper end of chamber 94. Similar to the operation of reed valve 32 depicted in FIG. 4, the central portion 44 of reed valve 32 is forced against face 72 and fluid can only flow through the pin hole 48. This serves to restrict the rate of flow back into the hose or tube upstream of the inlet nipple 18. Obviously, the pressure of the fluid in nipple 18 and in the upstream inlet tube or hose is sufficiently low to accept this retracted flow.

As is apparent from the foregoing the displacement of land 80 from the point of closing off flow to the outlet port 86 from the inlet port 76 increases the volume at the lower end of chamber 94 and creates a suction force to retract the residual fluid trapped in the line downstream of valve 60. The restricted flow flowing through reed valve 32 serves to limit the rate of travel of valve stem 64 to assure that the column of fluid in the line does not retract too quickly and cause a separation.

The trumpet/reed valve combination is particularly efficacious for a lens cleaning instrument adapted to clean the lens surface of an endoscope used in video, surgery. The description to follow immediately hereinbelow is a configuration where the trumpet/reed valve is disposed in the handle of the lens cleaning instrument which includes fluid retracting means for retracing the residual fluid trapped in the sheath surrounding and protecting the endoscope.

As best seen in FIGS. 9–14, the lens cleaning instrument generally illustrated by reference numeral 200 includes a double concentric tubular wall member defining a sheath consisting of outer tube 204 and inner tube 205 defining longitudinal passageways 206 separated by the wall portion 201, which is a by-product in the manufacturing process. Flow is admitted into the passageway at the distal end through the valve generally indicated by reference numeral 203 that serves to open and close to admit water from a source and includes means to retract the residual fluid trapped in the passageways 206 to space the fluid away from the outlet port 210. In this embodiment a cuff 208 including a plurality of circumferentially spaced vanes 211 serves to direct flow to flow over the transparent lens 214 fitted into the proximal end to bear against the distal end face of tube 202 and the inner diameter of 202 which serves as a pilot and to enclose the bottom portion and protect the endoscope 207 from being in contact with any fluid or body parts during an surgical operation or inspection. Tangs 116 serve to squarely position lens 214 to the face of the inner wall. 202, but other support means can be equally employed. The endoscope is adapted to slide through a central aperture in handle 140 and slide toward the distal end of lens cleaning instrument 200. The handle is a two piece configuration with a locking means (not shown) for locking the endoscope in place.

It is apparent from the foregoing that the lens cleaning instrument serves to protect the endoscope so that it virtually can be re-used without extensive sterilization for another operation or procedure in the operating room. As mentioned above, the one problem that has arisen with this type of instrument is that the residual trapped water when the water is shut-off is that a droplet at the end of the outlet port 210 could drip and migrate onto the lens and obstruct the vision of the viewer. The trumpet/reed valve 203 prevents this from occurring.

Figure 2:
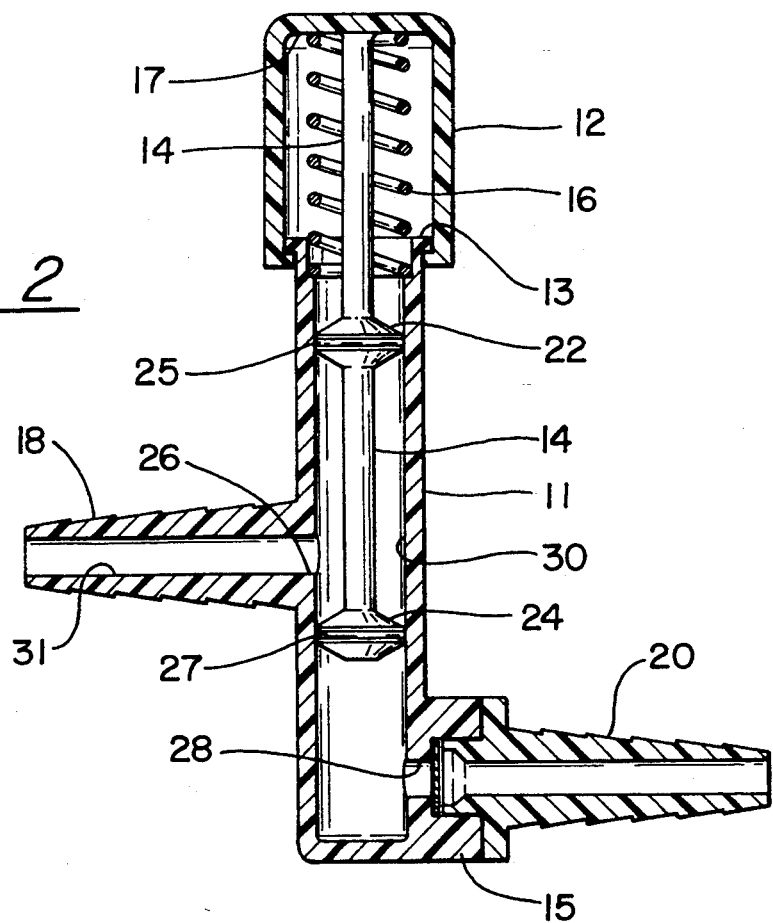
FIG. 2 is a sectional view in elevation taken through a longitudinal plane of the valve depicted in Fig. illustrating the valve in the normally closed position.
Figure 9:
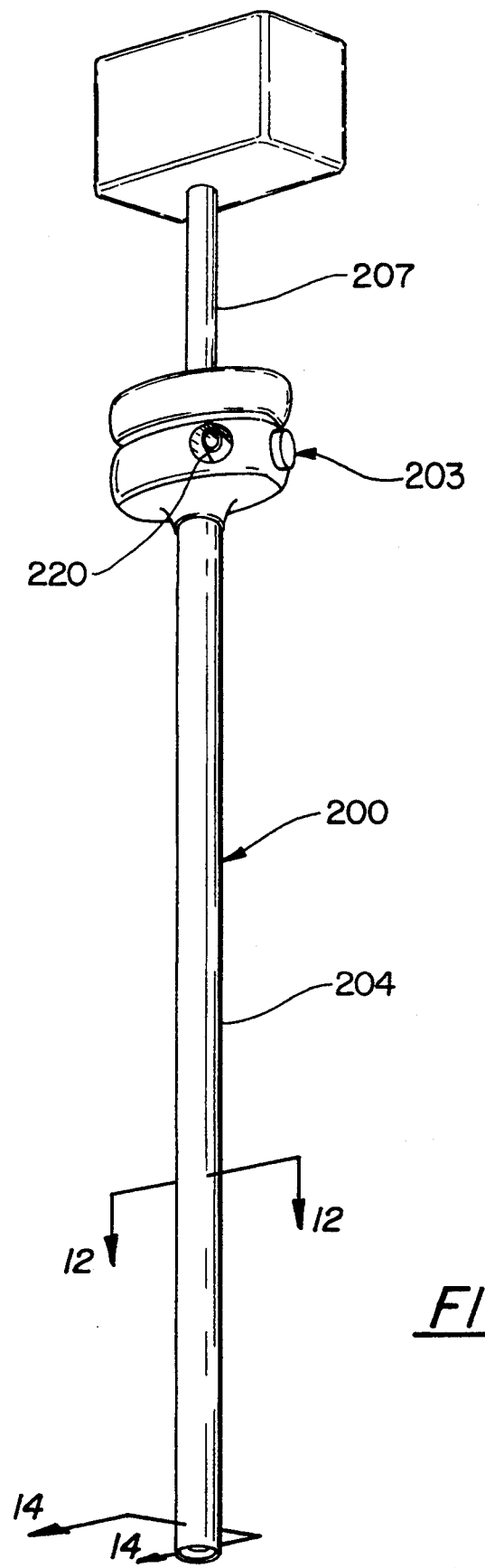
FIG. 9 is a perspective view of a lens cleaning apparatus utilizing the invention.
Figure 11:
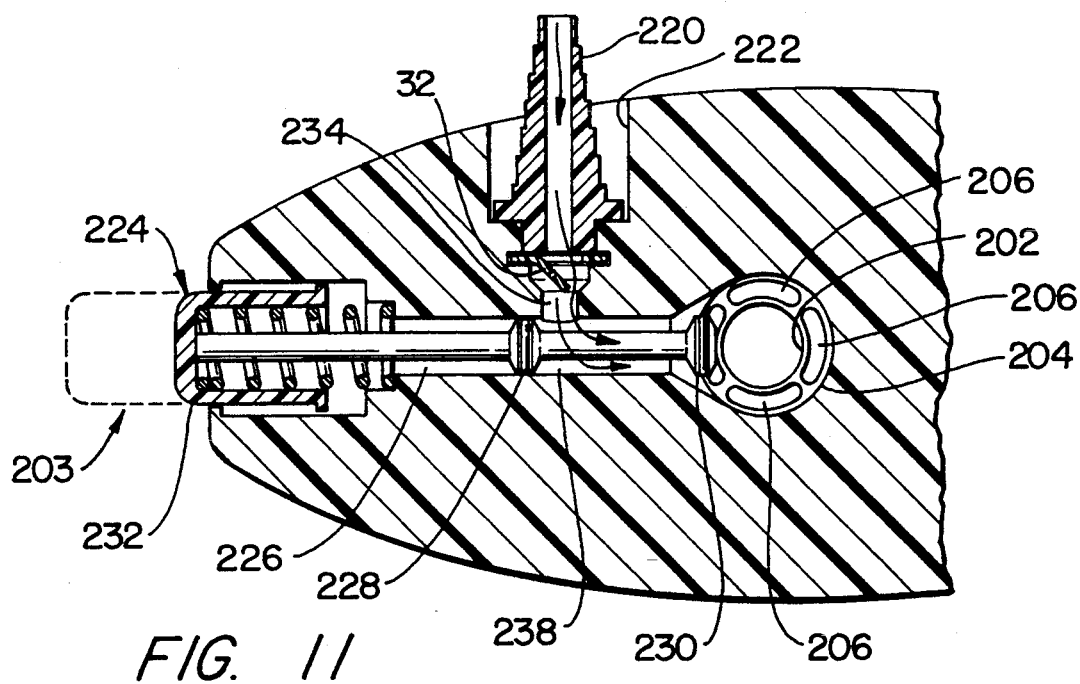
FIG. 11 is a sectional view taken along lines 11—11 of FIG. 10.
Figure 10:
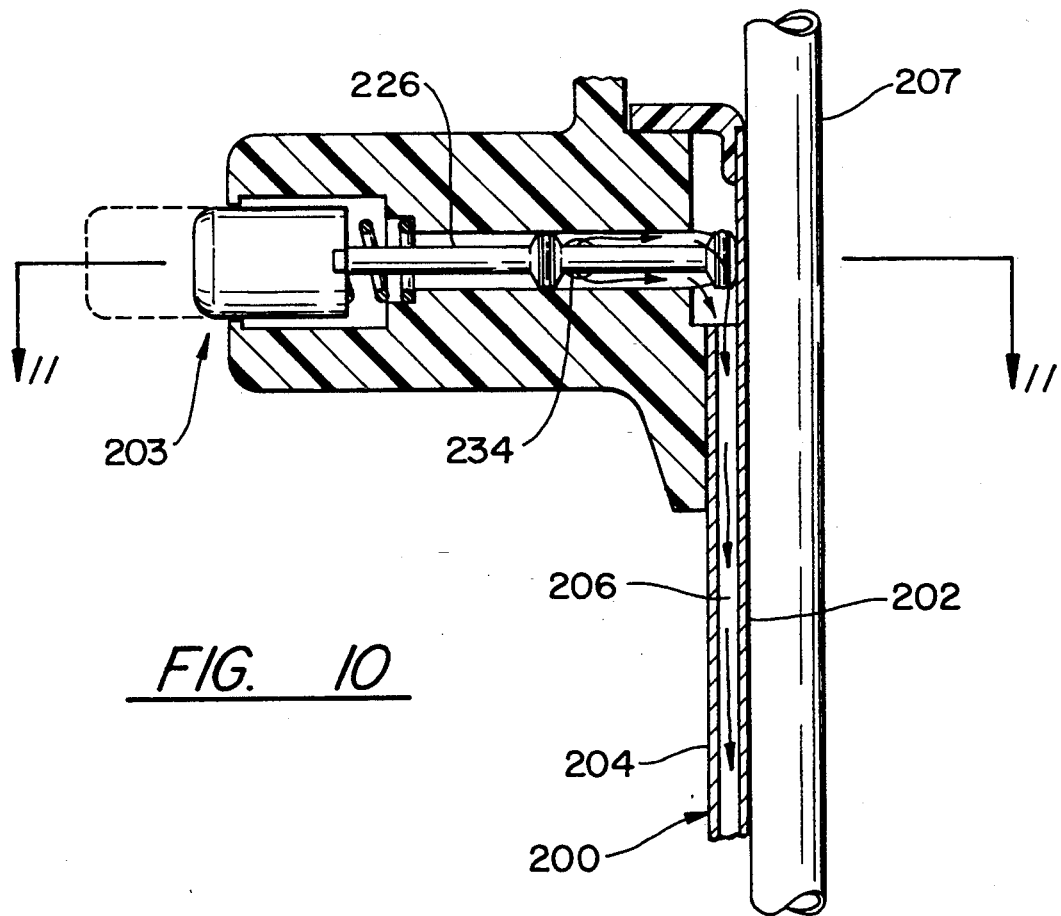
FIG. 10 is a partial view in section taken along the longitudinal axis of the trumpet/reed valve combination mounted in the handle of the lens cleaning apparatus of FIG. 9.
Figure 12:
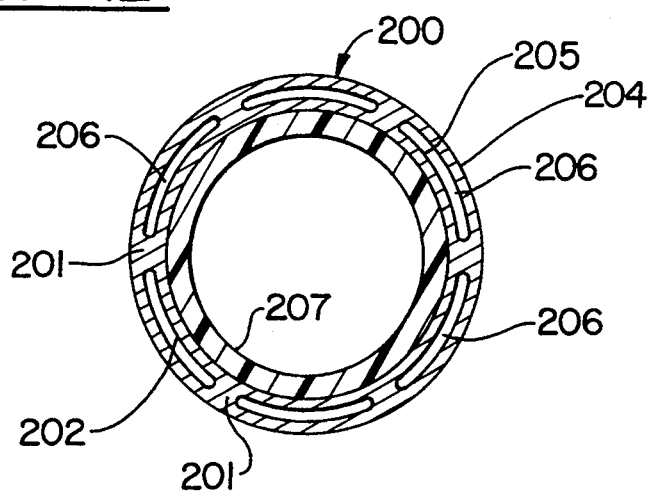
FIG. 12 is a sectional view taken along lines 12—12 of FIG. 9.
Figure 13:
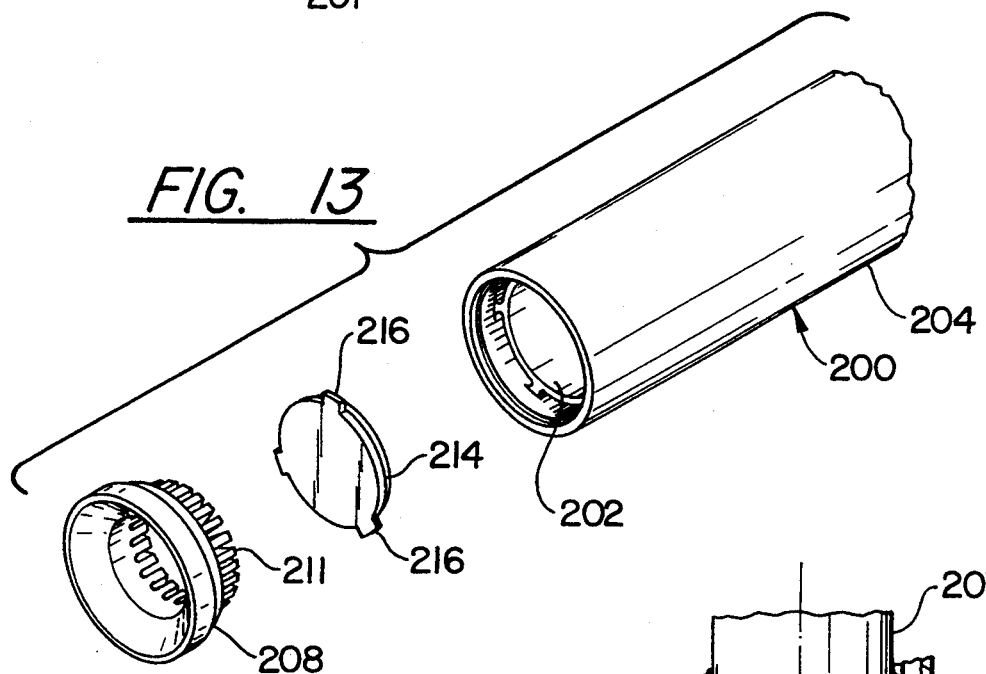
FIG. 13 is an exploded view in perspective illustrating the end closure of the lens cleaning sheath.
Figure 14:
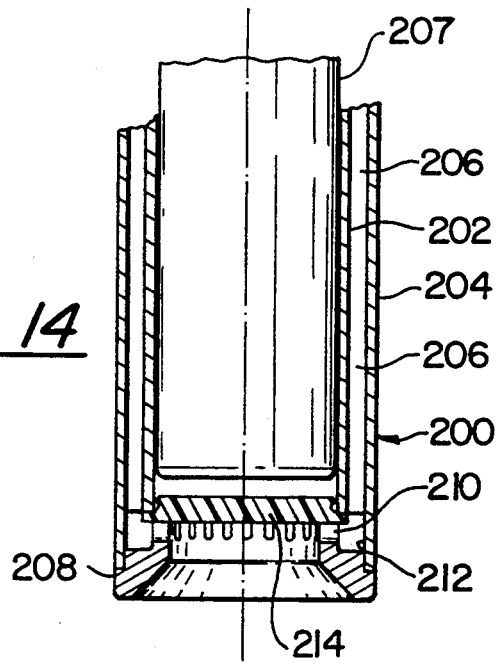
FIG. 14 is a partial view in section taken along the lines 14—14 of FIG. 9.

As noted in FIGS. 9-11 the inlet nipple 220 is trapped in recess 222 formed in the handle and clamps the thin walled circular reed valve 32 (FIG. 5) into place. The trumpet valve 224 which is similar in design and operation as the trumpet valve depicted in FIGS. 2, 3 and 4, is spring loaded in the upward position to close the valve and shut off the flow of fluid from inlet nipple 220. Trumpet valve 224 carries a central valve stem 226 having supported thereon a pair of axially spaced annular lands 228 and 230. Depressing the handle 232 forces the land 230 downwardly to uncover the inlet port 234 for admitting fluid into the valve cheer 238 to flow into the annular passage 206 of the tubular member 200 to effectuate the lens cleaning operation. Releasing the handle causes the valve stem 226 to return to the valve closed position by virtue of the spring which effectuates a retraction of the trapped fluid in the passage 206. The length of travel of land 230 in the retracting operation causes a suction action that serves to retract the trapped fluid. The reed valve is then forced by the pressure of the retracting fluid to seat against the end of the nipple 220 and hence become closed. The fluid then can only flow through the small orifice 48 (FIG. 5) to restrict the flow so as to prevent the fluid in the annular passage 206 from separating.

Figure 15:
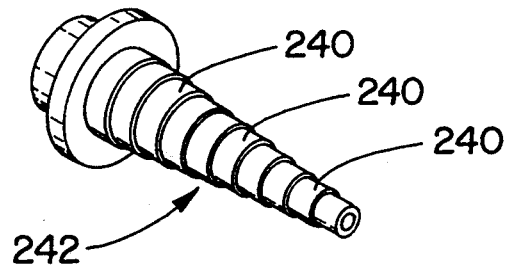
FIG. 15 is a perspective view of another nipple for use with this invention.

FIG. 15 is a perspective view of an alternate nipple that can be utilized with this invention and comprises a plurality of stepped incremental cylinders 240. These cylinders 240 define a cone 242 that creates adhesive retention cavities for securing the hose or tube being coupled thereto. This design affords manufacturing advantages since it is easily molded.

Figure 16:
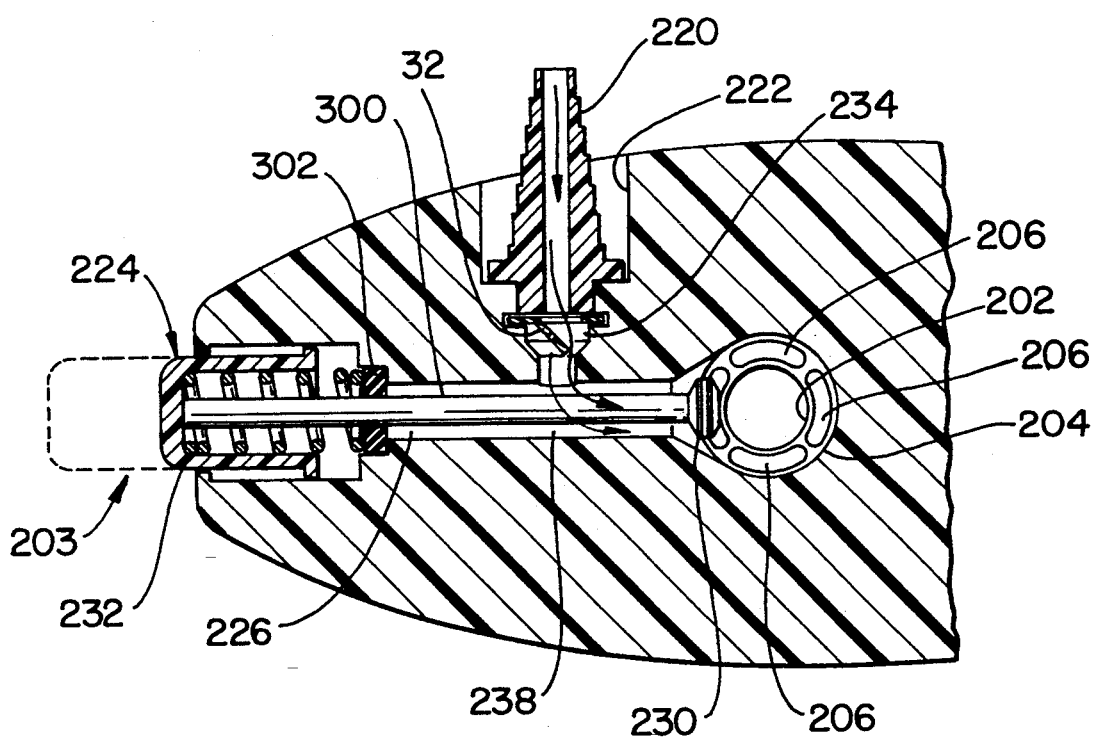
FIG. 16 is a sectional fragmentary view illustrating another embodiment of this invention utilizing another sealing arrangement for the trumpet valve.

FIG. 16 illustrates another version of the trumpet valve depicted in FIG. 11. The significant difference between the two embodiments is the way the valve stem is sealed. In FIG. 16, the valve stem 300 is identical to valve stem 226 (FIG. 11) except the land 228 is eliminated and seal 302 is inserted at the end of chamber 238. The seal may be any suitable packing, O-seal or the like fabricated from a suitable elastomeric material.

Although this invention has been shown and described with respect to detailed embodiments thereof, it will be appreciated and understood by those skilled in the art that various changes in form and detail thereof may be made without departing from the spirit and scope of the claimed invention.

It is claimed:

1. A combined on/off valve means and liquid fluid retraction means adapted to flow liquid fluid from a source to an output tube comprising a valve, body having a central bore, port means communicating with said central bore, a valve stem extending into said central bore and having an end portion extending beyond the valve body, a depressible handle attached to said end portion of said valve stem to urge said valve stem in one direction, spring means operatively connected to said depressible handle for urging said valve stem in an opposite direction, land means attached to said valve stem and moveable relative to said port means to block off the flow of liquid fluid in said opposite direction, valve means disposed in a recess formed in said valve body liquid fluidly connected to said port means for flowing the liquid fluid without restriction in one direction and flowing the liquid fluid with restriction in the opposite direction, and said land means having a predetermined stroke in said central bore beyond said port means for creating a suction when the liquid fluid is flowing in said opposite direction, whereby liquid fluid trapped in the output tube is retracted when the valve means moves toward the off position.

2. A combined on/off valve means and liquid fluid retraction means as claimed in claim 1 wherein said port means includes an inlet port and an outlet port and said valve means is a reed valve and is operatively connected to said outlet port.

3. A combined on/off valve means and liquid fluid retraction means as claimed in claim 1 wherein said port means includes an inlet port and an outlet port and said reed valve is operatively connected to said inlet port.

4. A combined on/off valve means and liquid fluid retraction means as claimed in claim 2 wherein said depressible handle is depressed to open said on/off valve means.

5. A combined on/off valve means and liquid fluid retraction means as claimed in claim 1 wherein the output tube is a double walled tube including at least one elongated passage and said double walled tube is adapted to encapsulate a portion around an endoscope to define a sheath, a handle on said sheath attached to the proximal end of said double walled tube, said combined on/off valve and liquid fluid retraction means disposed in said handle.

6. A combined on/off valve means and liquid fluid retraction means as claimed in claim 5 wherein said double walled tube includes an end enclosure means inserted at the distal end of said sheath and a cuff portion extending from said walled tube below the distal end of said sheath for flowing liquid fluid from said elongated passage beyond said sheath, redirecting said flow laterally relative to said elongated passage over said enclosure means.

7. A combined on/off valve means and liquid fluid retraction means as claimed in claim 6 including a plurality of elongated passages circumferentially spaced between the double walls of said double walled tube.

8. A combined on/off valve means and liquid fluid retraction means as claimed in claim 7 including a detachable nipple supported in a recess formed in said locking handle including a front end face for supporting said reed valve in said recess, said detachable nipple adapted to be connected to a liquid fluid conducting conduit for leading liquid fluid into said central bore of said valve body.

9. A combined on/off valve means and liquid fluid retraction means as claimed in claim 8 including a seal member supported in an annular groove formed on the periphery of said land means.

10. Liquid fluid retraction and on/off valve means adapted to flow liquid fluid from a source to an output tube comprising a valve body having a central bore, an inlet port and an outlet port communicating with said central bore, a valve stem extending into said central bore and having an end portion extending beyond the valve body, a depressible handle attached to said end portion of said valve stem to urge said valve stem to open said on/off valve means when moved in one direction, spring means operatively connected to said depressible handle for urging said valve stem in an opposite direction to close off said valve means, annular land means attached to said valve stem and moveable relative to said outlet port to block off the flow of liquid fluid in said opposite direction, a reed valve including a circular disk disposed in a recess formed in said valve body fluidly connected to said outlet port for flowing the liquid fluid without restriction when flow is from said inlet port to said outlet port and flowing the liquid fluid with restriction in the opposite direction when liquid fluid is flowing from said outlet port to said inlet port, and said annular land means having a predetermined stroke in said central bore extending beyond said outlet port for creating a suction when the liquid fluid is flowing into said inlet port through said reed valve when in the restriction mode, whereby liquid fluid trapped in the output tube is retracted when the valve means moves toward the off position.

11. Liquid fluid retraction and on/off valve means adapted to flow liquid fluid from a source to an output tube as claimed in claim 10 wherein said land means includes a pair of axially spaced annular lands.

12. Liquid fluid retraction and on/off valve means adapted to flow liquid fluid from a source to an output tube as claimed in claim 11 including sealing means attached to the outer periphery of each of said pair of annular lands.

13. Liquid fluid retraction and on/off valve means adapted to flow liquid fluid from a source to an output tube as claimed in claim 12 wherein said reed valve includes a central portion separated from the remaining portion along an arc and an aperture in the center of said central portion.

14. Liquid fluid retraction and on/off valve means adapted to flow liquid fluid from a source to an output tube as claimed in claim 13 wherein said depressible handle is fabricated from a flexible and resilient material and is opened on one end and closed on the opposite end, a pair of radially extending projections on the inner diameter adjacent said opened end, said valve body including an annular lip adapted to engage said pair of radially extending projections to prevent said depressible handle from becoming detached from said valve body, and said depressible handle being squeezeable to allow said projection from passing past said lip to remove said depressible handle.

15. Liquid fluid retraction and on/off valve means adapted to flow liquid fluid from a source to an output tube as claimed in claim 10 wherein said land means includes a valve element cooperating with the valve seat formed on one end of said bore for opening and closing said on/off valve and seal means formed at an opposite end of said bore and encircling said valve stem.

* * * * *